United States Patent
Lee

(10) Patent No.: US 9,113,993 B2
(45) Date of Patent: Aug. 25, 2015

(54) MESH PATCH FOR USE IN LAPAROSCOPIC HERNIA SURGERY

(76) Inventor: Jeongsam Lee, Gwang-ju (KR)

(*) Notice: Subject to any disclaimer, the term of this patent is extended or adjusted under 35 U.S.C. 154(b) by 615 days.

(21) Appl. No.: 13/482,012

(22) Filed: May 29, 2012

(65) Prior Publication Data

US 2012/0239063 A1  Sep. 20, 2012

Related U.S. Application Data

(63) Continuation-in-part of application No. PCT/KR2010/001413, filed on Mar. 6, 2010.

(30) Foreign Application Priority Data

Nov. 29, 2009 (KR) .................. 10-2009-0116301

(51) Int. Cl.
*A61B 17/08* (2006.01)
*A61F 2/02* (2006.01)
*A61F 2/00* (2006.01)

(52) U.S. Cl.
CPC ............ *A61F 2/0063* (2013.01); *A61F 2/0077* (2013.01); *A61F 2/0095* (2013.01); *A61F 2002/009* (2013.01); *A61F 2002/0072* (2013.01); *A61F 2002/0086* (2013.01)

(58) Field of Classification Search
CPC ............... A61B 17/12168; A61B 17/12177; A61B 17/122; A61B 17/0057; A61B 2017/0225; A61F 2/0063; A61F 2/0095; A61F 2/0009; A61F 2/0036; A61F 2/0077; A61F 2002/0068; A61F 2002/0072; A61F 2002/0086; A61F 2002/009
USPC ........ 606/1, 151, 213–215; 623/23.72, 23.74; 424/424, 425, 443, 444, 449; 602/52, 602/54, 57; 128/854, 855; 206/69, 363, 206/370, 438, 439, 440, 441, 570
See application file for complete search history.

(56) References Cited

U.S. PATENT DOCUMENTS

| | | | | |
|---|---|---|---|---|
| 3,068,863 A | * | 12/1962 | Bowman | 128/858 |
| 4,646,731 A | * | 3/1987 | Brower | 606/215 |
| 5,376,376 A | * | 12/1994 | Li | 424/443 |
| 5,593,441 A | * | 1/1997 | Lichtenstein et al. | 600/37 |
| 5,716,409 A | * | 2/1998 | Debbas | 606/151 |
| 5,840,052 A | * | 11/1998 | Johns | 602/54 |
| 6,120,539 A | * | 9/2000 | Eldridge et al. | 623/11.11 |
| 6,383,201 B1 | * | 5/2002 | Dong | 606/151 |

(Continued)

FOREIGN PATENT DOCUMENTS

KR  10-2006-0076252 A  7/2006

*Primary Examiner* — Ryan Severson
*Assistant Examiner* — Rachel S Papeika
(74) *Attorney, Agent, or Firm* — Sherr & Jiang, PLLC

(57) ABSTRACT

A mesh patch for a laparoscopic hernia surgery, which includes a flexible mesh, an adhesion layer surface, and an anti-adhesion layer surface. The flexible mesh is formed of a thin layer of filament using a biocompatible polymer. The adhesion layer surface is disposed on a front surface of the mesh. The adhesion layer surface is coated with an adhesion inducing material to be fixedly attached to a peritoneum. The anti-adhesion layer surface is disposed on a rear surface of the mesh. The anti-adhesion layer surface is coated with an anti-adhesion material so as not to adhere to intestines in an abdominal cavity. The protection film is detachably attached to the adhesion layer surface and the anti-adhesion layer surface to protect the mesh. Here, the protection film is easily detached by a laparoscopic instrument, and has an adhesive strength such that the mesh is unfolded upon detaching.

8 Claims, 6 Drawing Sheets

(56) References Cited

U.S. PATENT DOCUMENTS

| | | | |
|---|---|---|---|
| 6,736,823 B2 * | 5/2004 | Darois et al. | 606/151 |
| 6,790,213 B2 * | 9/2004 | Cherok et al. | 606/151 |
| 6,912,733 B2 * | 7/2005 | Carrafield et al. | 2/209 |
| 7,011,688 B2 * | 3/2006 | Gryska et al. | 623/23.72 |
| 7,156,804 B2 * | 1/2007 | Nicolo | 600/37 |
| 7,404,819 B1 * | 7/2008 | Darios et al. | 606/151 |
| 7,935,046 B2 * | 5/2011 | Chu | 600/30 |
| 2001/0049539 A1 | 12/2001 | Rehil | |
| 2002/0049503 A1 * | 4/2002 | Milbocker | 623/23.72 |
| 2005/0021058 A1 * | 1/2005 | Negro | 606/151 |
| 2006/0025785 A1 * | 2/2006 | Cully et al. | 606/151 |
| 2006/0083767 A1 * | 4/2006 | Deusch et al. | 424/422 |
| 2007/0219568 A1 | 9/2007 | Yeo et al. | |
| 2008/0033461 A1 | 2/2008 | Koeckerling et al. | |
| 2008/0109017 A1 * | 5/2008 | Herweck et al. | 606/151 |
| 2008/0139877 A1 * | 6/2008 | Chu et al. | 600/30 |
| 2008/0147200 A1 * | 6/2008 | Rousseau et al. | 623/23.75 |
| 2008/0243149 A1 | 10/2008 | Kockerling et al. | |
| 2009/0082792 A1 * | 3/2009 | Koyfman et al. | 606/151 |
| 2009/0134044 A1 * | 5/2009 | Wish | 206/69 |
| 2009/0234461 A1 | 9/2009 | Rehnke | |
| 2010/0104608 A1 * | 4/2010 | Abuzaina et al. | 424/400 |
| 2010/0292717 A1 * | 11/2010 | Petter-Puchner et al. | 606/151 |

\* cited by examiner

MESH PATCH FOR USE IN LAPAROSCOPIC HERNIA SURGERY

CROSS-REFERENCE TO RELATED APPLICATIONS

This U.S. non-provisional patent application is a Continuation-In-Part Application of PCT International Application No. PCT/KR2010/001413 (filed on Mar. 6, 2010), which claims priority under 35 U.S.C. §119 of Korean Patent Application No. 10-2009-0116301 (filed on Nov. 29, 2009), which are all hereby incorporated by reference in their entirety.

BACKGROUND

The present disclosure herein relates to a mesh patch for use in a laparoscopic hernia surgery.

Generally, insertion-type mesh patches are being widely used for curing the inguinal and ventral hernia. These patches are permanently implanted in patient's body. U.S. Pat. No. 5,824,082 discloses a prosthesis for use in hernia repair surgery having a preformed prosthetic fabric supported along its periphery by a shape memory alloy wire having a transformation temperature corresponding to normal body temperature allowing the prosthesis to be tightly rolled into a cylindrical configuration for delivery through a laparoscopic instrument.

U.S. Pat. No. 5,824,082 provides a hernia repair mesh patch supported by a wire strand of nitinol frame to facilitate a laparoscopic treatment. The patch can be rolled and inserted into a cannula, and is unfolded inside the body through the cannula to cover the direct and indirect hernia region.

However, in U.S. Pat. No. 5,824,082, since the prosthetic fabric supported along its periphery by a shape memory alloy has to be inserted in a cylindrical shape, a cannula having a significant size is needed.

A trocar having a smaller diameter is less hazardous and painful for patients.

Accordingly, there is a need of a sufficiently flexible hernia mesh that can be woven in advance in accordance with the anatomical configuration, can be easily unfolded when released from a tubular laparoscopic introducer, can be maintained at a desired location without any stapling or stitching of fascia disposed thereunder, and can be inserted or rolled into a trocar having a smaller diameter.

In the Total Extraperitoneal Repair (TEP) that is being widely used, a mesh patch including monofilament is being used as the flexible patch for the hernia surgery, but three laparoscopic trocars are needed, and stripping of extraperitoneal tissue, stripping of hernia sac, and fixation of a mesh by a special tacker need to be performed.

During the surgery, extraperitoneal tissue needs to be handled, and plenty of time is needed for stripping of hernia sac and prevention of postoperative complications such as injury of vas deferens, hematoma, abnormal sense, and pain.

As shown in FIG. 1, a mesh currently used in TEP is configured with only a monofilament 301 or a multifilament.

Also, as shown in FIG. 2, although there is a product coated with an anti-adhesion agent 302, it is rarely used in recent years, and has been very occasionally used only for incisional hernia or umbilical hernia.

SUMMARY

The present disclosure provides a mesh patch which can be easily attached to an affected part through a single port and can be promptly unfolded during a laparoscopic hernia surgery.

The present disclosure also provides a flexible hernia mesh patch which can be easily unrolled or unfolded through a single port during a laparoscopic surgery, can be fixedly attached without any stapling or stitching of fascia, and can be rolled or folded to be inserted into a wound retractor for securing a passage through the umbilicus or trocar.

Embodiments of the present disclosure provide mesh patches for a laparoscopic hernia surgery, including: a flexible mesh formed of a thin layer of filament using a biocompatible polymer; an adhesion layer surface on a front surface of the mesh, the adhesion layer surface being coated with an adhesion inducing material to be fixedly attached to a peritoneum; an anti-adhesion layer surface on a rear surface of the mesh, the anti-adhesion layer surface being coated with an anti-adhesion material so as not to adhere to intestines in an abdominal cavity; and a protection film detachably attached to the adhesion layer surface and the anti-adhesion layer surface to protect the mesh, wherein the protection film is easily detached by a laparoscopic instrument, and has an adhesive strength such that the mesh is unfolded upon detaching.

In some embodiments, the protection film may include: a central protection film including a central part detachably attached to a central portion of the adhesion layer surface and a connection part extending from one side of the central part to one side edge of the mesh; and a peripheral protection film detachably attached to the anti-adhesion layer surface and the adhesion layer surface except the central part.

In other embodiments, the central protection film may include a lower surface attached to the adhesion layer surface and an upper surface folded at the other side of the central part to cover an upper portion of the lower surface. An end of an upper surface of the connection part may be attached to the side edge. A holder portion grippable by the laparoscopic instrument may be disposed at the end of the upper surface.

In still other embodiments, the peripheral protection film may include four quadrant protection films attached to an upper right side, a lower right side, an upper left side, and a lower left side of the anti-adhesion layer surface and the adhesion layer surface, respectively. The quadrant protection film may cover one quarter surface of the anti-adhesion layer surface and an extension surface thereof may be folded at a boundary dividing the adhesion layer surface into four except the central part to be formed on the adhesion layer surface in two fold. An end of an upper quadrant protection film formed in two fold may be attached to one edge of the adhesion layer surface. A holder portion grippable by the laparoscopic instrument may be disposed at the end of the upper quadrant protection film.

In even other embodiments, the peripheral protection film may include two bisected protection films attached to an upper side and a lower side or a right side and a left side of the anti-adhesion layer surface and the adhesion layer surface, respectively. The bisected protection film may cover one half surface of the anti-adhesion layer surface and an extension surface thereof may be folded at a boundary dividing the adhesion layer surface into two except the central part to be formed on the adhesion layer surface in two fold. An end of an upper bisected protection film formed in two fold may be attached to one edge of the adhesion layer surface. A holder portion grippable by the laparoscopic instrument may be disposed at the end of the upper quadrant protection film.

In yet other embodiments, the peripheral protection film may include one integral protection films attached to a front surface and a rear surface of the anti-adhesion layer surface and the adhesion layer surface. The integral protection film may be attached to a whole surface of the anti-adhesion layer surface and both extension surfaces thereof may be folded in a vertical or horizontal direction at a boundary dividing the adhesion layer surface into two except the central part to be formed on the adhesion layer surface in two fold. An end of an upper integral protection film formed in two fold may be attached to upper and low edges or right and left edges of the adhesion layer surface. A holder portion grippable by the laparoscopic instrument may be disposed at the end of the upper integral protection film.

In further embodiments, a portion folded at the boundary of the adhesion layer surface may be attached while allowing a small overlapping portion around the boundary.

In still further embodiments, the mesh patches may further include a holder strip disposed on the holder portion and grippable by the laparoscopic instrument.

In even further embodiments, the mesh patches may further include a holder strip disposed at other side of the edge of the peripheral protection film where the holder portion is not formed and grippable by the laparoscopic instrument.

In yet further embodiments, the central part may be circular.

BRIEF DESCRIPTION OF THE DRAWINGS

The accompanying drawings are included to provide a further understanding of the present disclosure, and are incorporated in and constitute a part of this specification. The drawings illustrate exemplary embodiments of the present disclosure and, together with the description, serve to explain principles of the present disclosure. In the drawings.

DETAILED DESCRIPTION

Exemplary embodiments of the present disclosure will be described below in more detail with reference to the accompanying drawings. The present disclosure may, however, be embodied in different forms and should not be construed as limited to the embodiments set forth herein. Rather, these embodiments are provided so that this disclosure will be thorough and complete, and will fully convey the scope of the present disclosure to those skilled in the art.

Hereinafter, exemplary embodiments of the present disclosure will be described in detail with reference to the accompanying drawings.

Figure 1:
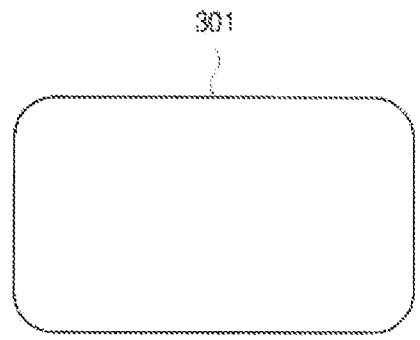
FIGS. 1 and 2 are views of typical meshes.
Figure 2:
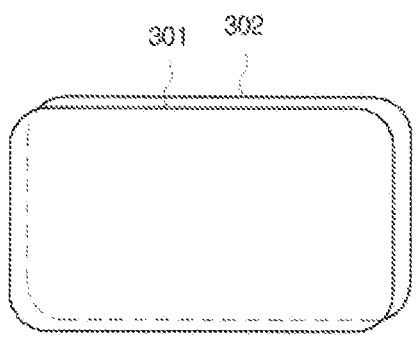
Figure 3:
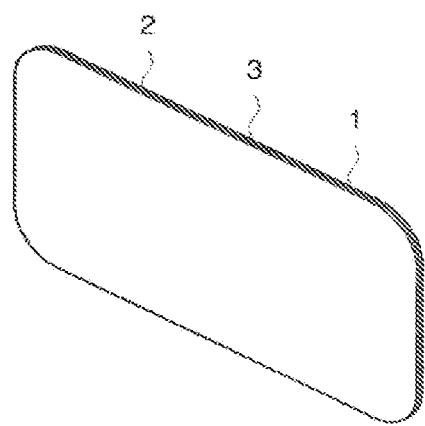
FIG. 3 is a view illustrating a structure of a mesh according to an embodiment of the present disclosure.

FIG. 3 is a view illustrating a structure of a mesh according to an embodiment of the present disclosure.

The mesh, which is a biocompatible polymer, may include polypropylene, polyethylene, polyolefin such as copolymer of propylene and ethylene, polyamide such as nylon 6 and nylon 66, polyurethane, fluoropolymer such as polyvinylidene fluoride, and polyester, preferably, one of copolymer of ethylene and propylene or polypropylene.

In one embodiment, the mesh may be formed of polpropylene monofilament or polyester multifilament. The mesh may be manufactured to have flexibility, as shown in FIG. 3, have a rectangular laminated shape.

Since an adhesion inducing material that is an adhesive is coated on the front surface 2 of the mesh, the mesh may be strongly attached to a desired part of peritoneum.

The adhesion inducing material according to an embodiment of the present disclosure may include typical and verified adhesion inducing materials against body membrane such as cell adhesive in which a functional peptide is combined with a mussel adhesion protein, cyanoacrylate adhesive, fibrin glue, gelatin glue, polyurethane adhesive, and Tachocomb.

An anti-adhesion agent may be coated on the rear surface 3 of the mesh.

Since the anti-adhesion agent is coated on the mesh, the rear surface may not adhere to intestines in the abdominal cavity during or after operation.

The adhesion protection materials may include typical and verified anti-adhesion materials against human membranes such as nano fiber anti-adhesion agent, oxidized regenerated cellulose formulation that is polysaccharide, sodium hyaluronate (HA) formulation, sodium carboxymethyl cellulose (CMC) formulation, dextran formulation, and GUARDIX-SL solution.

Figure 4:
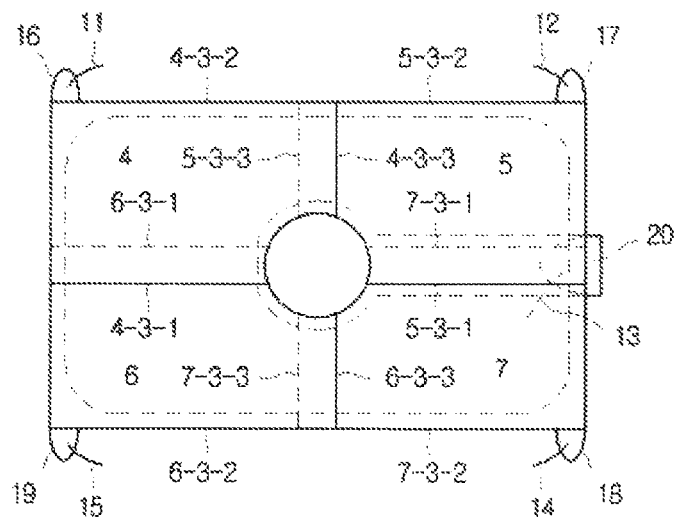
FIG. 4 is a cross-sectional view of a mesh patch according to an embodiment of the present disclosure.
Figure 12:
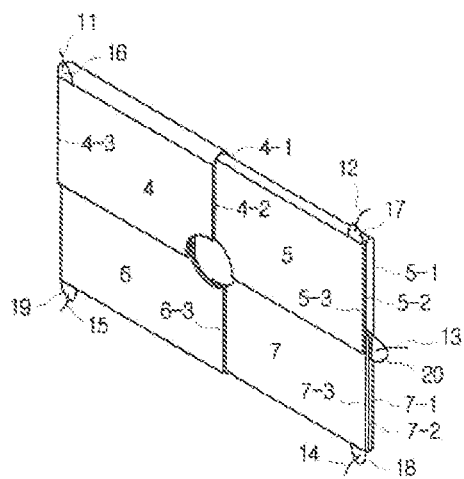

FIG. 4 is a cross-sectional view illustrating a protection film attached to a mesh. FIG. 12 is a view illustrating a whole structure of a mesh patch used in a hernia surgery according to an embodiment of the present disclosure.

As described above, the mesh patch according to the embodiment of the present disclosure may include a mesh 1 (multifilament polyester or monofilament polypropylene mesh) that is a basic framework, an adhesive layer surface 2 coated with an adhesion inducing material on the front surface of the mesh 1 such that the mesh can be strongly adhered to the peritoneum, and an anti-adhesion layer surface 3 coated with an anti-adhesion agent on the rear surface of the mesh such that the mesh does not adhere to the organs in the abdominal cavity.

The mesh 1 may be formed into a mesh patch which includes a protection film detachable to maintain the mesh 1 in the abdominal cavity and allow a desired work.

The protection film may be attached to the adhesion layer surface 2 and the anti-adhesion layer surface 3 to protect the mesh 1, and may be easily detached. When the protection film is detached, the adhesion layer surface 2 of the mesh 1 coated with an adhesion inducing material may have weak adhesion strength sufficient to maintain adhesion and be unfolded in the abdominal cavity.

Figure 5:
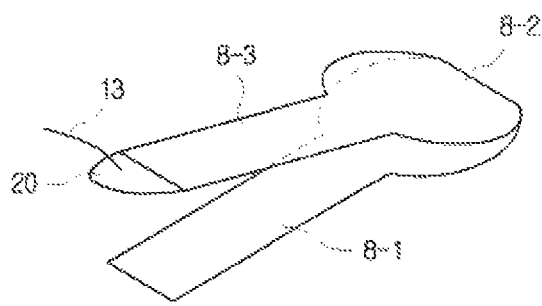
FIG. 5 is a view illustrating a structure of a central protection film according to an embodiment of the present disclosure.
Figure 6:
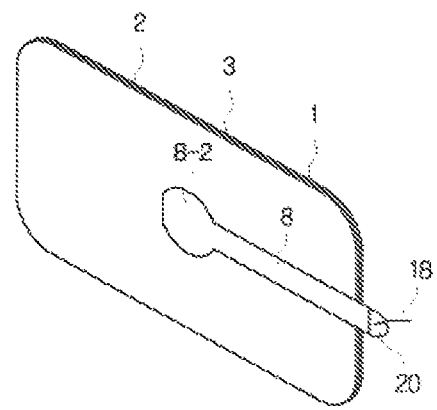
FIG. 6 is a view illustrating a central protection film attached to a mesh according to an embodiment of the present disclosure.

FIG. 4 is a cross-sectional view of a mesh patch according to an embodiment of the present disclosure. FIG. 5 is a view illustrating a structure of a central protection film according to an embodiment of the present disclosure. FIG. 6 is a view illustrating a central protection film attached to a mesh according to an embodiment of the present disclosure.

As shown in FIGS. 4 through 6, the protection film may be configured to have a central portion 8-2 attached to the central portion of the adhesion layer surface 2, and a connection portion 8-3 extending from one side of the central portion 8-2 to the edge of the one side of the mesh 1. The protection film may include a central protection film 8 that is detachably attached, peripheral protection films 4, 5, 6 and 7 that is detachably attached to the anti-adhesion layer surface 3 and the adhesion layer surface 2 except the central portion thereof.

The central protection film 8 may be configured to have a lower surface 8-1 attached to the adhesion layer surface 2 and an upper surface 8-3 covering the upper portion of the lower layer while being unfolded at the other one side of the central portion. The end of the upper surface 8-3 of the connection portion may be attached to the edge of the one side, and a holder portion 20 grippable by a laparoscopic instrument may be formed at the end of the upper surface.

The upper surface 8-3 and the lower surface 8-1 may have a sufficiently weak adhesive strength such that the mesh can be unrolled when the rolled mesh patch is detached.

In another embodiment, a hold strip 17 gripped and pulled by the laparoscopic instrument may be further disposed at the end of the holder portion 20.

As described above, since the lower surface 8-1 and the upper surface 8-3 overlaps each other, when the holder portion 20 formed on the upper surface 8-3 is pulled, the lower surface of the hold portion 20 attached to the adhesion layer surface can be easily detached.

Figure 13:
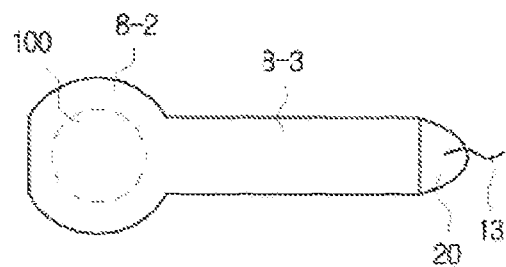
FIGS. 13 and 14 are views illustrating a process of stripping a central protection film according to an embodiment of the present disclosure.
Figure 14:
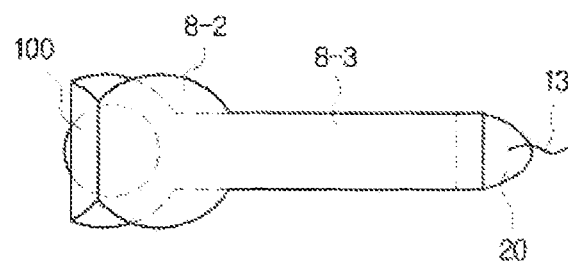

FIGS. 13 and 14 illustrate a process in which the central protection film is detached according to an embodiment of the present disclosure.

When a holder strip 13 of a central protection film 8 is gripped and pulled by a laparoscopic instrument as shown in FIG. 13, the folded portion of the central portion 8-2 of the central protection film 8 may be unfolded and detached to allow an adhesion layer surface 2 of a central portion 100 to be exposed.

Although the central portion 8-2 is formed to have a circular shape in one embodiment, the central portion 8-2 may also be manufactured in various shapes such as quadrangular or hexagonal shapes, showing equal effects, respectively.

In a first embodiment of the present disclosure, the central protection film 8 may be detachably attached, and then the peripheral protection film may be attached.

Figure 7:
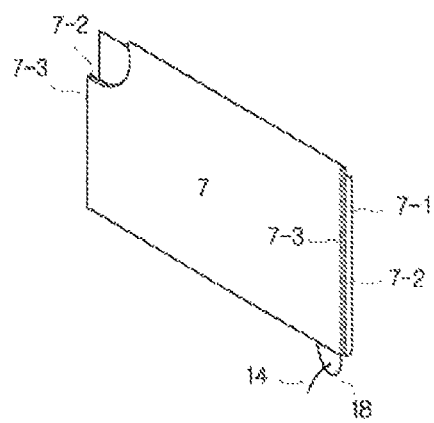
FIG. 7 is a view illustrating a structure of a peripheral protection film according to a first embodiment of the present disclosure.

FIG. 7 is a view illustrating a structure of a peripheral protection film according to a first embodiment of the present disclosure. FIGS. 8 through 12 are views illustrating a process of attaching a peripheral protection film according to a first embodiment of the present disclosure The peripheral protection film may also have a weak adhesive strength such that the mesh can be unfolded when detached.

The peripheral protection film may include first to fourth peripheral protection films 4, 5, 6 and 7 that are attached to the first to fourth quadrants of the anti-adhesion layer surface 3 and the adhesion layer surface 2.

The quadrant protection films may be formed in two-fold, in which one quadrant of the anti-adhesion layer surface 3 and the extension surface thereof are folded at the quadrant boundary of the adhesion layer surface 2 other than the central portion.

The end of the upper quadrant protection film 7-3 that is formed in two-fold may be attached to one edge of the adhesion layer surface.

As described above, the peripheral protection films may have a weak adhesive strength such that the peripheral protection films can be easily detached with a weak force and the mesh can be easily unrolled.

The quadrant protection film may be attached to the central portion of the anti-adhesion layer surface at the end thereof, may be folded toward the adhesion layer surface at the edge of the mesh. The extension portion may be folded from the adhesion layer surface to the folded film upper portion 7-3 while excluding the central portion of the central protection film (7-2), allowing the other end to be integrally attached as a singly film at the edge of the adhesion layer surface.

The quadrant protection film may be divided into first to fourth peripheral protection film, i.e., upper right, lower right, upper left, and lower left, respectively.

Referring to FIG. 7, one end of a second peripheral protection film 7 attached to the lower right surface corresponding to one quarter of the whole may be attached from the central portion of the anti-adhesion layer surface 3 to the center of the right edge thereof (7-1), and may be folded toward the adhesion layer surface 2 at the lower edge of the mesh (7-2). The extension portion may be folded toward the upper portion of the folded film 7-2 on the line 7-3-1 extending from the central portion of the adhesion layer surface 2 to the right edge thereof except the area of the central portion 8-2, allowing the other end to be integrally attached as a single film at the lower edge 7-3-2 of the adhesion layer surface 2.

A holder portion 18 that can be gripped and unfolded by a laparoscopic instrument may be formed at the other end portion 7-3-2 of the lower side.

In another embodiment, a holder strip 14 that can be gripped and unfolded by a laparoscopic instrument may be further provided to the holder portion 18.

In another embodiment, a holder strip (not shown) that can be gripped and unfolded by a laparoscopic instrument may be further provided at one side of the other end portion 7-3-2.

As described above, since configured to be folded toward the upper portion of the folded film 7-2 on the line 7-3-1 extending from the central portion 100 of the adhesion layer surface 2 to the right edge thereof except the area of the central portion 8-2, when the holder portion 18 formed at the end 7-3-2 of the folded upper surface is pulled by a laparoscopic instrument, a portion of the folded film 7-2 attached to the adhesion layer surface may be easily detached from the adhesion layer surface 2.

Thereafter, the film portion 7-1 attached to the anti-adhesion layer surface 3 may be more easily detached due to the characteristics of the anti-adhesion layer surface 3 coated with an anti-adhesion agent.

The fourth peripheral protection film 5 may be configured similarly to the second peripheral protection film 7 except a difference in vertical, direction.

Figure 9:
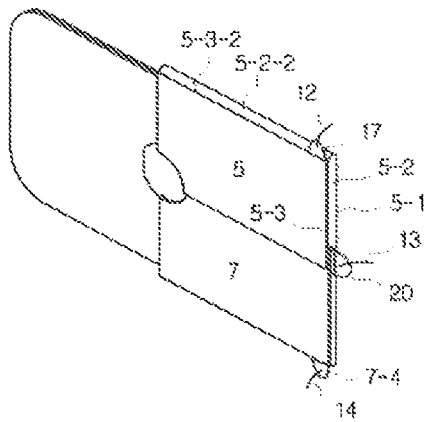

Referring to FIGS. 4 and 9, one end of a first peripheral protection film 5 attached to the upper right surface corresponding to one quarter of the whole may be attached from the central portion of the anti-adhesion layer surface 3 to the center of the right edge thereof (5-1), and may be folded toward the adhesion layer surface 2 at the upper edge of the mesh (5-2). The extension portion may be folded toward the upper portion of the folded film 5-2 on the line 5-3-1 extending from the central portion of the adhesion layer surface 2 to the right edge thereof except the area of the central portion 8-2, allowing the other end 5-3-2 to be integrally attached as a single film at the upper edge of the adhesion layer surface 2.

A holder portion 17 that can be gripped and unfolded by a laparoscopic instrument may be formed at the other end portion 5-3-2 of the lower side.

In another embodiment, a holder strip 12 that can be gripped and unfolded by a laparoscopic instrument may be further provided to the holder portion 17.

In another embodiment, a holder strip (not shown) that can be gripped and unfolded by a laparoscopic instrument may be further provided at one side of the other end portion 5-3-2.

FIG. 9 is a view illustrating two peripheral protection films attached among four peripheral protection films.

The first peripheral protection film 6 may be configured similarly to the second peripheral protection film 7 except a difference in horizontal direction.

Figure 10:
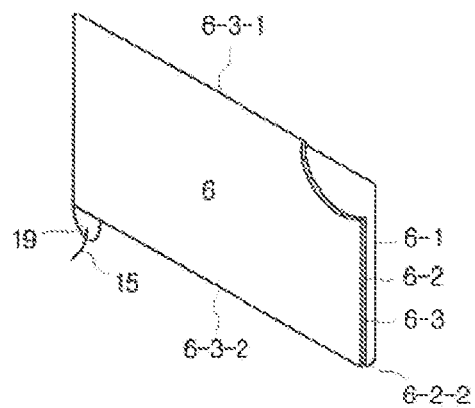

Referring to FIGS. 4 and 10, one end of a fourth peripheral protection film 6 attached to the lower left surface corresponding to one quarter of the whole may be attached from the central portion of the anti-adhesion layer surface 3 to the center of the left edge thereof (6-1), and may be folded toward the adhesion layer surface 2 at the lower left edge of the mesh (6-2). The extension portion may be folded toward the upper portion of the folded film 6-2 on the line 6-3-1 extending from the central portion of the adhesion layer surface 2 to the right edge thereof except the area of the central portion 8-2, allowing the other end 6-3-2 to be integrally attached as a single film at the upper edge of the adhesion layer surface 2.

A holder portion 19 that can be gripped and unfolded by a laparoscopic instrument may be formed at the other end portion 6-3-2 of the lower side.

In another embodiment, a holder strip 15 that can be gripped and unfolded by a laparoscopic instrument may be further provided to the holder portion 19.

In another embodiment, a holder strip (not shown) that can be gripped- and unfolded by a laparoscopic instrument may be further provided at one side of the other end portion 6-3-2.

Figure 11:
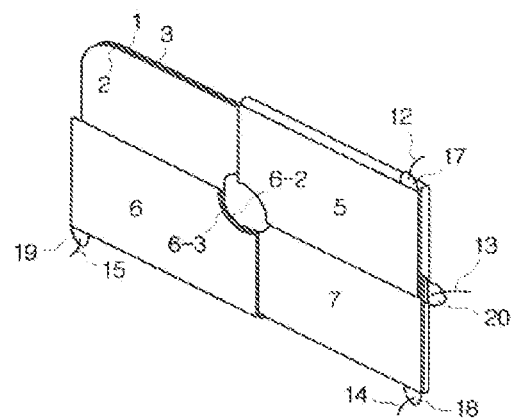

FIG. 11 is a view illustrating three peripheral protection films attached among four peripheral protection films.

The second peripheral protection film 4 may be configured similarly to the first peripheral protection film 6 except a difference in vertical direction.

Referring to FIGS. 4 and 12, one end of a third peripheral protection film 4 attached to the upper left surface corresponding to one quarter of the whole may be attached from the central portion of the anti-adhesion layer surface 3 to the center of the left edge thereof (4-1), and may be folded toward the adhesion layer surface 2 at the upper left edge of the mesh (4-2). The extension portion may be folded toward the upper portion of the folded film 4-2 on the line 4-3-1 extending from the central portion of the adhesion layer surface 2 to the right edge thereof except the area of the central portion 8-2, allowing the other end 4-3-2 to be integrally attached as a single film at the upper edge of the adhesion layer surface 2.

A holder portion 16 that can be gripped and unfolded by a laparoscopic instrument may be formed at the other end portion 4-3-2 of the lower side.

In another embodiment, a holder strip 11 that can be gripped and unfolded by a laparoscopic instrument may be further provided to the holder portion 16.

In another embodiment, a holder strip (not shown) that can be gripped and unfolded by a laparoscopic instrument may be further provided at one side of the other end portion 4-3-2.

The holder portion 16 may be configured to be folded toward the anti-adhesion layer surface.

Hereinafter, a process of performing an operation using a mesh path for a hernia surgery according to an embodiment of the present disclosure will be described below.

First, after making an incision around the umbilicus, a wound retractor may be mounted to input a laparoscopic instrument.

After checking the hernia site through the laparoscopic instrument, intestines or serous membranes held in the hernia sac may be restored to their original location.

Next, a mesh patch for a laparoscopic hernia surgery according to an embodiment of the present disclosure may be rolled into the incision of the umbilicus, and then the central portion 100 of the mesh may be located around the hernia sac. Thereafter, a holder strip 13 attached to the holder portion 20 of the central protection film protruding between peripheral protection films may be pulled out Due to the pulling force, a portion of the holder 20 may be easily gripped by the laparoscopic instrument.

The holder portions 15, 16, 17, 18 and 20 may be configured to be folded toward the anti-adhesion layer surface, facilitating the manipulation of the adhesive surface of the central portion.

As described above, since the central protection film 8 is folded at the one side of the central portion 8-2 and is attached extending to the edge of the one side of the mesh, as shown in FIGS. 13 and 14, when the holder portion 13 of the central protection film 8 is pulled, the mesh patch may be unfolded, allowing the central protection film 8 covering the adhesion layer surface of the central portion 100 to be separated.

Thereafter, when the adhesion layer surface of the central portion 100 is adhered closely to the peritoneum around the hernia sac, the adhesion layer surface of the central portion 100 among a portion 2 coated with an adhesion inducing material may be strongly attached to the peritoneum around the hernia sac.

Next, when the holder portions 15, 16, 17 and 18 or the holder strips 11, 12, 13 and 14 of the first to fourth peripheral protection films are sequentially pulled out, the peripheral protection films of the adhesion layer surface 2 may be detached, and then the protection films of the anti-adhesion layer surface 3 that is a portion of the mesh coated with an adhesion inducing material may be detached, allowing the mesh to be unfolded and thus strongly attached to the peritoneum around the hernia sac.

The detached central protection film 8 and the first to fourth protection films may be extracted to the outside of the human body, and only the mesh according to the embodiment may be strongly attached around the hernia sac.

Since the anti-adhesion layer surface that is the rear surface of the mesh is coated with an anti-adhesion agent, as described above, the mesh may be prevented from being attached to other portions even after the protection films are detached.

In another embodiment, the central portion 100 may be marked on the anti-adhesion layer surface 3 and the adhesion layer surface 2.

As described above, by marking the central portion 100, an operator may exactly attach the central portion 8-2 of the central protection film 8 to the marked central portion 100.

In the first embodiment of the present disclosure, the central protection film 8 and the four peripheral protection films 4, 5, 6 and 7 have been exemplified, but in another embodiment, one central protection film and two peripheral protection films 30 and 31 may be applied.

Figure 15:
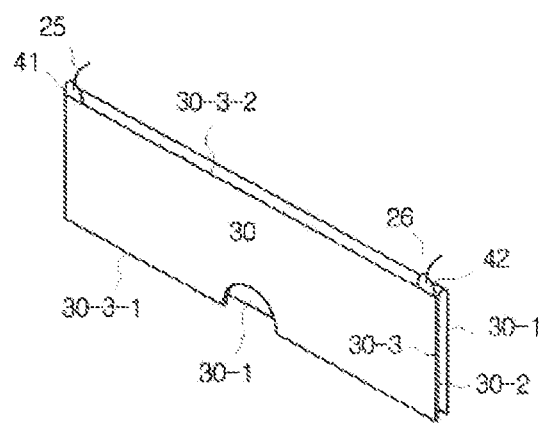
FIG. 15 is a view illustrating a structure of a peripheral protection film according to a second embodiment of the present disclosure.
Figure 16:
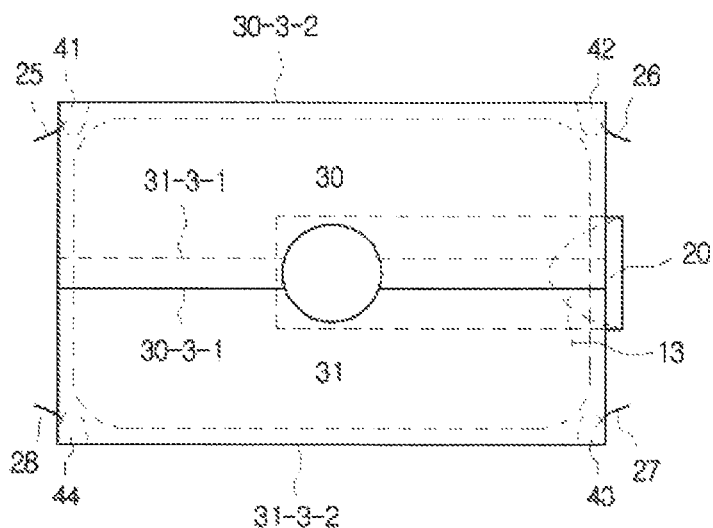
FIG. 16 is a cross-sectional view illustrating a peripheral protection film attached according to a second embodiment of the present disclosure.

FIGS. 15 and 16 illustrate a cross-section of a mesh patch for a laparoscopic hernia surgery including one central protection film 8 and two peripheral protection films 30 and 31 according to a second embodiment of the present disclosure.

In the second embodiment, the central protection film 8 may be configured similarly to that of FIG. 6, and then an upper peripheral protection film 30 and a lower peripheral protection film 31 may be attached to a bisected surface.

Although the surface is bisected into upper and lower in FIGS. 15 and 16, the peripheral protection film may be attached to right and left sides of the adhesion layer surface and the anti-adhesion layer surface.

The bisected protection film divided into two surfaces may cover a half surface of the anti-adhesion layer surface and then the extension surface thereof may be folded at boundaries 30-3-1 and 31-3-1 dividing the adhesion layer surface into two while excluding the central portion 8-2. The bisected protection film may be formed in two fold on the adhesion layer, and the end of the upper bisected protection film may be attached to one edge 31-3-2 and 30-3-2 of the adhesion layer surface.

Referring again to FIGS. 15 and 16, one end of an upper peripheral protection film 30 attached to the upper surface corresponding to one half of the whole may be attached from the edge of the left center to the edge of the right center at the central portion of the anti-adhesion layer surface 3 of the mesh coated with an anti-adhesion agent (30-1), and may be folded toward the adhesion layer surface 2 at the upper edge of the mesh (30-2). The extension portion may be folded toward the upper portion of the folded film 30-2 on the line 30-3-1 extending from the central portion of the adhesion layer surface 2 to the right and left edges thereof except the area of the central portion 8-2, allowing the other end 30-3-2 to be integrally attached as a single film at the upper edge of the adhesion layer surface 2.

Holder portions 41 and 42 that can be gripped and unfolded by a laparoscopic instrument at both sides thereof may be formed at the other end portion 30-3-2 of the upper side.

In another embodiment, holder strips 25 and 26 that can be gripped and unfolded by a laparoscopic instrument may be further provided to the holder portions 41 and 42.

In another embodiment, a holder strip (not shown) that can be gripped and unfolded by a laparoscopic instrument may be further provided at one side of the other end portion 30-3-2.

The lower peripheral protection film 31 may be configured similarly to the first peripheral protection film 30 except a difference in vertical direction.

Referring again to FIG. 16, one end of a lower peripheral protection film 31 attached to the lower surface corresponding to one half of the whole may be attached from the edge of the left center to the edge of the right center at the central portion of the anti-adhesion layer surface 3 of the mesh coated with an anti-adhesion agent (31-3-1), and may be folded toward the adhesion layer surface 2 at the lower edge of the mesh. The extension portion may be folded toward the upper portion of the folded film on the line 31-3-1 extending from the central portion of the adhesion layer surface 2 to the right and left edges thereof except the area of the central portion 8-2, allowing the other end 31-3-2 to be integrally attached as a single film at the lower edge of the adhesion layer surface 2.

Holder portions 43 and 44 that can be gripped and unfolded by a laparoscopic instrument at both sides thereof may be formed at the other end portion 31-3-2 of the lower side.

In another embodiment, holder strips 27 and 28 that can be gripped and unfolded by a laparoscopic instrument may be further provided to the holder portions 43 and 44.

In another embodiment, a holder strip (not shown) that can be gripped and unfolded by a laparoscopic instrument may be further provided at one side of the other end portion 31-3-2.

As shown in FIG. 16, the portion 30-3-1 of the upper peripheral protection film 30 folded on the line extending right and left central edges, and the portion 31-3-1 of the lower peripheral protection film 31 folded thereon may be attached while overlapping each other at the boundary therebetween.

Also, the hold portion 20 of the central protection film 8 may be outwardly protruded and folded at the right edge of the overlapping portion of the upper peripheral protection film 30 and the lower peripheral film 31.

In a process of performing an operation using a mesh path for a hernia surgery according to a second embodiment of the present disclosure, the central protection film 8 may be detached, and then the adhesion layer surface of the central portion 100 may be adhered closely to the peritoneum around the hernia sac. Thus, the adhesion layer surface of the central portion 100 of the adhesion layer surface 2 coated with an adhesion inducing material may be strongly attached to the peritoneum around the hernia sac.

The holder portions 41, 42, 43 and 44 according to a second embodiment of the present disclosure may be configured to be folded toward the anti-adhesion layer surface such that an operator can easily perform the attaching process after the adhesion surface of the central portion is attached.

Thereafter, when the holder portions 41, 42, 43 and 44 are pulled out via the holder strips 25, 26, 27 and 28 of the upper and lower peripheral protection films 30 and 31, the protection film may be detached from the adhesion layer surface 2, and then the adhesion layer surface 2 coated with an adhesion inducing material may be unfolded to be strongly attached to the peritoneum around the hernia sac.

A mesh patch according to a third embodiment of the present disclosure may be configured with one central protection film and one peripheral protection film 60

Figure 17:
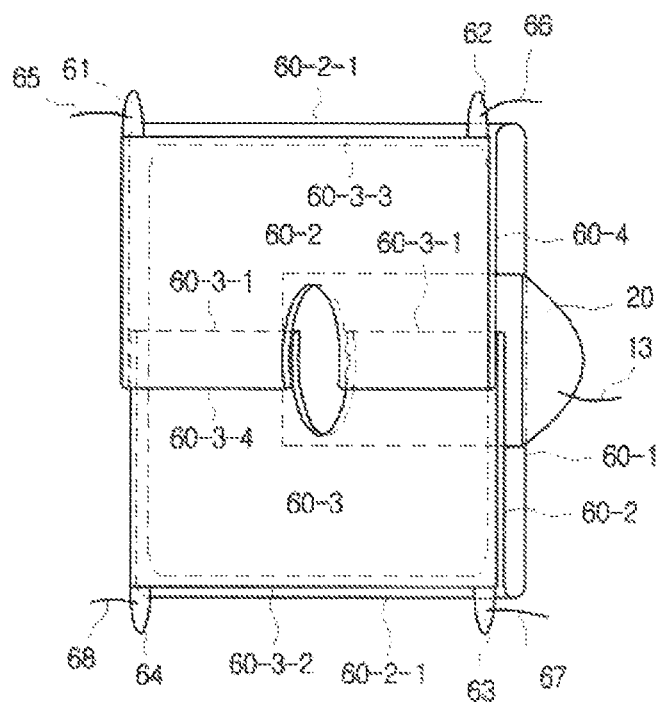
FIG. 17 is a view illustrating a structure of a peripheral protection film attached according to a third embodiment of the present disclosure.

FIG. 17 is a cross-sectional view illustrating a mesh patch for laparoscopic hernia surgery including one central protection film 8 and one peripheral protection film 60 according to a third embodiment of the present disclosure.

Figure 8:
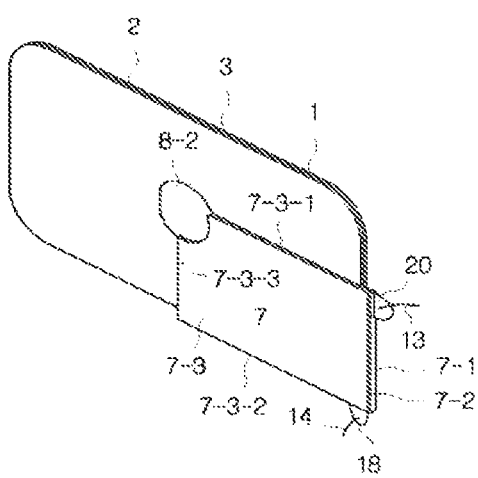
FIGS. 8 through 12 are views illustrating a process of attaching a peripheral protection film according to a first embodiment of the present disclosure.

The central protection film 8 of FIG. 17 may be configured similarly to that of FIG. 8, and may be first attached.

Referring to FIG. 17, one end of the protection film may be disposed at the lower edge 60-3-2 of an adhesion layer surface 2 of a mesh coated with an adhesion inducing material. The extension surface 60-3 thereof may be folded on the line 60-3-1 extending from the left edge to the right edge at the lower end of the central portion 8-2, and may be folded under the folded film to be attached to the undersurface of the adhesion layer surface 2 (60-2) while the central portion 8-2 is be excluded so as not to cover the central portion 8-2 of the central protection film. The extension portion may be folded at the lower edge 60-2-1 to extend and cover the whole surface of the anti-adhesion layer surface 3 of the mesh coated with an anti-adhesion agent (60-1)

The protection film extending to cover the whole surface of the anti-adhesion layer surface 3 may be folded at the upper edge 60-2-1 to be attached to the upper portion of the adhesion layer surface 2 of the mesh, and the extension surface thereof may be folded on the line 60-3-4 extending from the left edge to the right edge at the upper end of the central portion 21. The extension surface may be folded on the folded film 60-4 excluding the central portion 21 so as not to cover the central portion 8-2 of the central protection film 8, and the other end of the extension portion may be attached to the upper edge 60-3-3 for a finish.

The peripheral protection film 60 according to the third embodiment of the present disclosure may be configured to be attached as a single film.

The peripheral protection film may be formed as one integral protection film on the adhesion layer surface and the anti-adhesion layer surface.

The integral protection film may be attached to the whole surface of the anti-adhesion layer surface. Both extension surfaces of the integral protection film may overlap each other at the boundary bisecting the adhesion layer surface except the central portion 8-2. The ends 60-2-1 and 60-3-2 of the upper integral protection film formed in two-fold may be attached to the upper and lower edges of the adhesion layer surface, respectively, and holder portions 61, 62, 63 and 64 that can be gripped by a laparoscopic instrument may be disposed at the ends of the integral protection film, respectively.

In the third embodiment, although the integral protection film has been described as folded in the vertical direction, the integral protection film may be folded in the horizontal direction.

The portion of the peripheral protection film 60 folded at the central portion may be attached while allowing small overlapping portions 60-3-1 and 60-3-4 at the boundary.

Also, a holder portion 20 of the end of the central protection film 8 may be outwardly protruded and folded at the right edge of the portion folded while allowing the overlapping portions 60-3-1 and 60-3-4.

At one end and the other end of the peripheral protection film 60, holder portions 61, 62, 63 and 64 may be disposed at one end of right and left sides, and holder strips 65, 66, 67 and 68 may be disposed at the holder portions 61, 62, 63 and 64, respectively.

In a process of performing an operation using a mesh path for a hernia surgery according to a third embodiment of the present disclosure, the central protection film 8 may be detached, and then the adhesion layer surface of the central portion 100 may be adhered closely to the peritoneum around the hernia sac. Thus, the adhesion layer surface of the central portion 100 of the adhesion layer surface 2 coated with an adhesion inducing material may be strongly attached to the peritoneum around the hernia sac.

Thereafter, when the holder portions are pulled out via the holder strips of the peripheral protection films 60, the adhesion layer surface may be detached, and then the whole of the adhesion layer surface 2 coated with an adhesion inducing material may be unfolded to be strongly attached to the peritoneum around the hernia sac.

A mesh patch according to an embodiment of the present disclosure can be easily located and attached to an affect part through a single port during a laparoscopic hernia surgery, and can be promptly unrolled or unfolded.

A mesh patch according to an embodiment of the present disclosure can be easily unrolled or unfolded through a single port during a laparoscopic surgery, can be fixedly attached without any stapling or stitching of fascia, and can be rolled or folded to be inserted into a wound retractor for securing a passage through the umbilicus or trocar.

A mesh patch according to an embodiment of the present disclosure is not unnecessarily adhered to other intestines in the abdominal cavity due to an anti-adhesion layer surface, and can be strongly attached to an affected part due to an adhesion inducing material layer on the opposite surface.

Also, since a mesh patch according to an embodiment of the present disclosure can be flexibly rolled or folded, the mesh patch can be easily rolled into a wound retractor for securing a passage through the umbilicus or a trocar.

Furthermore, when a mesh patch according to an embodiment of the present disclosure is used in a hernia surgery, the surgery can be performed using a single port through the umbilicus that is an incisional site without leaving a scar. Also, since handling of extraperitoneal tissue is rarely needed, the surgery time can be surely shortened, and the postoperative complications can be significantly reduced.

The above-disclosed subject matter is to be considered illustrative and not restrictive, and the appended claims are intended to cover all such modifications, enhancements, and other embodiments, which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A mesh patch for use in a laparoscopic hernia surgery, comprising:
    a flexible mesh formed of a thin layer of filament using a biocompatible polymer;
    an adhesion layer surface on a front surface of the mesh, the adhesion layer surface being coated with an adhesion inducing material to be fixedly attached to a peritoneum;
    an anti-adhesion layer surface on a rear surface of the mesh, the anti-adhesion layer surface being coated with an anti-adhesion material so as not to adhere to intestines in an abdominal cavity; and
    a protection film detachably attached to the adhesion layer surface and the anti-adhesion layer surface to protect the mesh,
    wherein the protection film is detachable by a laparoscopic instrument, and has an adhesive strength such that the mesh is unfolded upon detaching,
    wherein the protection film comprises:
    a central protection film comprising a central part detachably attached to a central portion of the adhesion layer surface and a connection part extending from one of the central part to one side edge of the mesh; and
    a peripheral protection film detachably attached to the anti-adhesion layer surface and the adhesion layer surface except the central part,
    wherein:
    the central protection film comprises a lower surface attached to the adhesion layer surface and an upper surface folded at the other side of the central part to cover an upper portion of the lower surface;
    an end of an upper surface of the connection a is attached to the side edge; and
    a holder portion grippable by the laparoscopic instrument is disposed at the end of the upper surface.

2. The mesh patch of claim 1, further comprising a holder strip disposed on the holder portion and grippable by the laparoscopic instrument.

3. The mesh patch of claim 1, wherein the central part is circular.

4. A mesh patch for use in a laparoscopic hernia surgery, comprising:
    a flexible mesh formed of a thin layer of filament using a biocompatible polymer;
    an adhesion layer surface on a front surface of the mesh, the adhesion layer surface being coated with an adhesion inducing material to be fixedly attached to a peritoneum;
    an anti-adhesion layer surface on a rear surface of the mesh, the anti-adhesion layer surface being coated with an anti-adhesion material so as not to adhere to intestines in an abdominal cavity; and
    a protection film detachably attached to the adhesion layer surface and the anti-adhesion layer surface to protect the mesh, wherein the protection film is detachable by a laparoscopic instrument, and has an adhesive strength such that the mesh is unfolded upon detaching, wherein the protection film comprises:

a central protection film comprising a central art detachably attached to a central portion of the adhesion layer surface and a connection part extending side of the central part to one side edge of the mesh; and a peripheral protection film detachably attached to the anti-adhesion layer surface and the adhesion layer surface except the central part, wherein:

the peripheral protection film comprises four quadrant protection films attached to an upper right side, a lower right side, an upper left side, and a lower left side of the anti-adhesion layer surface and the adhesion layer surface, respectively;

each of the four quadrant protection films covers one quarter surface of the anti-adhesion layer surface and an extension surface thereof is folded at a boundary dividing the adhesion layer surface into four except the central part to be formed on the adhesion layer surface in two fold;

an end of at least one of the upper left side quadrant protection film or the upper right side quadrant protection film is formed in two fold and is attached to one edge of the adhesion layer surface; and a holder portion grippable by the laparoscopic instrument is disposed at the end of the upper quadrant protection film.

5. The mesh patch of claim 4, wherein a portion folded at the boundary of the adhesion layer surface is attached while allowing a small overlapping portion around the boundary.

6. The mesh patch of claim 5, further comprising a holder strip disposed at other side of the edge of the peripheral protection film where the holder portion is not formed and grippable by the laparoscopic instrument.

7. A mesh patch for use in a laparoscopic hernia surgery, comprising:

a flexible mesh formed of a thin layer of filament using a biocompatible polymer;

an adhesion layer surface on a front surface of the mesh the adhesion layer surface being coated with an adhesion inducing material to be fixedly attached to a peritoneum;

an anti-adhesion layer surface on a rear surface of the mesh, the anti-adhesion layer surface being coated with an anti-adhesion material so as not to adhere to intestines in an abdominal cavity; and a protection film detachably attached to the adhesion layer surface and the anti-adhesion layer surface to protect the mesh, wherein the protection film is detachable by a laparoscopic instrument, and has an adhesive strength such that the mesh is unfolded upon detaching, wherein the protection film comprises:

a central protection film comprising a central part detachably attached to a central portion of the adhesion layer surface and a connection part extending from one side of the central art to one side edge of the mesh; and a peripheral protection film detachably attached to the anti-adhesion layer surface and the adhesion layer surface except the central part, wherein:

the peripheral protection film comprises two bisected protection films attached to an upper side and a lower side or a right side and a left side of the anti-adhesion layer surface and the adhesion layer surface, respectively;

the bisected protection film covers one half surface of the anti-adhesion layer surface and an extension surface thereof is folded at a boundary dividing the adhesion layer surface into two except the central part to be formed on the adhesion layer surface in two fold;

an end of a bisected protection film formed in two fold is attached to one edge of the adhesion layer surface; and a holder portion grippable by the laparoscopic instrument is disposed at the end of the bisected protection film.

8. A mesh patch for use in a laparoscopic hernia surgery, comprising:

a flexible mesh formed of a thin layer of filament using a biocompatible polymer;

an adhesion layer surface on a front surface of the mesh the adhesion layer surface being coated with an adhesion inducing material to be fixedly attached to a peritoneum;

an anti-adhesion layer surface on a rear surface of the mesh, the anti-adhesion layer surface being coated with an anti-adhesion material so as not to adhere to intestines in an abdominal cavity; and a protection film detachably attached to the adhesion layer surface and the anti-adhesion layer surface to protect the mesh, wherein the protection film is detachable by a laparoscopic instrument and has an adhesive strength such that the mesh is unfolded upon detaching, wherein the protection film comprises:

a central protection film comprising a central part detachably attached to a central portion of the adhesion layer surface and a connection part extending from one side of the central part to one side edge of the mesh; and a peripheral protection film detachably attached to the anti-adhesion layer surface and the adhesion layer surface except the central part, wherein:

the peripheral protection film comprises one integral protection film attached to a front surface and a rear surface of the anti-adhesion layer surface and the adhesion layer surface;

the integral protection film is attached to a whole surface of the anti-adhesion layer surface and both extension surfaces thereof are folded in a vertical or horizontal direction at a boundary dividing the adhesion layer surface into two except the central part to be formed on the adhesion layer surface in two fold;

an end of the integral protection film formed in two fold is attached to upper and low edges or right and left edges of the adhesion layer surface; and a holder portion grippable by the laparoscopic instrument is disposed at the end of the integral protection film.

* * * * *